United States Patent [19]

Arakawa et al.

[11] Patent Number: 4,753,867

[45] Date of Patent: Jun. 28, 1988

[54] OPTICAL RECORDING MEDIUM

[75] Inventors: Seiichi Arakawa; Hirofumi Kondo; Nobutoshi Asai; Junetsu Seto, all of Kanagawa, Japan

[73] Assignee: Sony Corporation, Tokyo, Japan

[21] Appl. No.: 821,040

[22] Filed: Jan. 22, 1986

[30] Foreign Application Priority Data

Jan. 24, 1985 [JP] Japan ................................. 60-11307

[51] Int. Cl.$^4$ .............................................. G03C 1/733
[52] U.S. Cl. ................................ 430/345; 430/337; 430/962
[58] Field of Search ............... 430/945, 345, 962, 337; 549/24, 25

[56] References Cited

U.S. PATENT DOCUMENTS 4,565,779  1/1986  Arakawa et al. .................... 430/962

OTHER PUBLICATIONS

Becker, et al.: "Photochromism: Spectroscopy and Photochemistry of Pyran and Thiopyran Derivatives", Photochromism, vol. 72, No. 3, Mar. 1968, pp. 997–1001.

*Primary Examiner*—Won H. Louie
*Attorney, Agent, or Firm*—Hill, Van Santen, Steadman & Simpson

[57] ABSTRACT

An optical recording medium including a substrate and a photosensitive layer thereon, the photosensitive layer containing as its major ingredients, the combination of a polymeric binder resin and an indolinospirobenzothiopyran compound represented by the general formula (I):

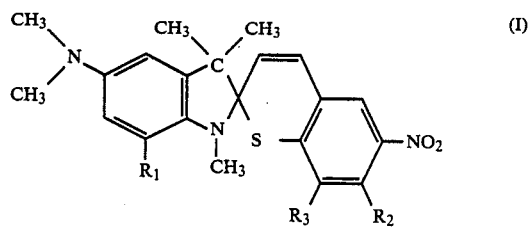

where $R_1$, $R_2$ and $R_3$ are each a hydrogen atom, a halogen atom, an alkyl group containing from 1 to 5 carbon atoms, an alkoxy group containing from 1 to 5 carbon atoms, an alkoxymethyl group containing from 1 to 5 carbon atoms in the alkoxy group, a hydroxymethyl group or an alkylaminomethyl group containing 2 to 6 carbon atoms in the alkyl group. The optical recording medium has a colored image which is very stable against heat and visible light.

9 Claims, 2 Drawing Sheets

OPTICAL RECORDING MEDIUM

BACKGROUND OF THE INVENTION

1. Field of the Invention

The present invention relates to an optical recording medium with a colored image which is stable against heat and visible light.

2. Description of the Prior Art

Photochromic compounds are known for forming colored images upon irradiation with ultraviolet rays. A typical example of a photochromic organic compound which is currently being used is a spiropyran compound. When a spiropyran compound is used as a photochromic material, the spiropyran compound is dispersed or dissolved in a polymer serving as a binder resin and is formed into a film or coated on a base. Such a conventional photochromic material becomes colored upon irradiation with ultraviolet rays and then returns to its initial colorless state upon heating or irradiation with visible light. Since a photochromic material containing a spiropyran compound has such interesting properties, a variety of applications for different recording materials, copying materials, and display materials have been attempted with such compounds.

However, the conventional photochromic compound is not thermally stable in a colored state. The colored compound gradually fades even at room temperature and its colored state cannot be maintained for a long period of time. Even when the photochromic compound is exposed to visible light, its colored state is lost. Thus, when the photochromic image must be kept for a long period of time, it must be shielded from visible light. When an optical recording medium using a conventional photochromic material is utilized for enlarging and projecting a photochromic image, the image is discolored by the light from the light source within a short period of time. For this reason, current applications of optical recording media using conventional spiropyran compounds are limited.

SUMMARY OF THE INVENTION

In order to solve the problems described, the present inventors have developed an optical recording medium exhibiting a colored image which has high thermal stability not heretofore achieved by conventional optical recording media of this type, and which is stable against visible light.

The present invention provides an optical recording medium having a photosensitive layer of a photosensitive composition containing, as its major constituents, a polymeric resin serving as a binder and an indolinospirobenzothiopyran compound represented by the general formula (I) given below:

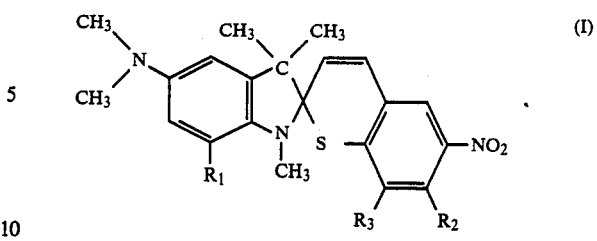

where $R_1$, $R_2$ and $R_3$ are a hydrogen atom, a halogen atom, an alkyl group having from 1 to 5 carbon atoms, an alkoxy group having from 1 to 5 carbon atoms, an alkoxymethyl group having from 1 to 5 carbon atoms, a hydroxymethyl group, or an alkylaminomethyl group containing from 2 to 6 carbon atoms in its alkyl group.

The polymeric binder material may be any one of a number of resins which have good compatibility with the compound represented by general formula (I) and have excellent film-forming properties. Such polymer material may include resins such as polymethyl methacrylate, polystyrene, polyvinyl acetate, polyvinyl butyral, cellulose acetate, polyvinyl chloride, polyvinylidene chloride, vinyl chloride-vinylidene chloride copolymers, vinyl chloride-vinyl acetate copolymers, polypropylene, polyethylene, polyacrylonitrile, urethane resins, epoxy resins, polyester resins, phenolic resins, and phenoxy resins. From that group of materials, a polymer containing chlorine or a phenolic resin is preferred.

In the photosensitive composition, the amount of the compound represented by the general formula (I) may be 20 to 120 parts by weight per 100 parts by weight of the polymeric binder resin.

In addition to the improved photosensitive material of the present invention, the photosensitive composition may contain a phenol such as bisphenol A, an antioxidant such as a hindered phenol, hindered amine and nickel complex; a photostabilizer; and a heat curing or photocuring agent. The photosensitive composition preferably contains an organic acid salt of cobalt, manganese, zinc or the like such as cobalt naphthenate or zinc naphthenate.

The photosensitive composition is dissolved in a polymeric material by a process known to those skilled in the art and is then formed into a film or coated as a photosensitive layer on a substrate, thereby providing an optical recording medium.

The substrate material may be a material such as a polyacrylate, polyethylene terephthalate, cellulose acetate, polycarbonate, normal paper, baryta paper, glass, or a metal.

A reflecting layer made of Al, Cr, Ag, or Au may be formed on the upper or lower surface of the photosensitive layer in the optical recording medium of the present invention. A protecting film may be formed on the photosensitive layer directly or through a reflecting layer.

The present invention also is directed to an optical recording medium which has been heat treated after coloring of the photosensitive layer by irradiation with ultraviolet rays in a predetermined pattern.

The temperature and time of heat treatment vary in accordance with the type of photosensitive composition, but generally will be in the range from 80° C. to 120° C. for times ranging from several tens of minutes (20 or so) to several hours (2 to 10 hours, for example).

When a reflecting layer is formed on the photosensitive layer and the base for the colored photosensitive layer comprises an ultraviolet-shielding material, the nonimage portion of the photosensitive layer is not subjected to the photochromic effect even if ultraviolet rays are allowed to irradiate the nonimage portion. Therefore, a high contrast between the image and non-image portions can be maintained for a period of long-term storage.

DESCRIPTION OF THE PREFERRED EMBODIMENTS

Figure 1:
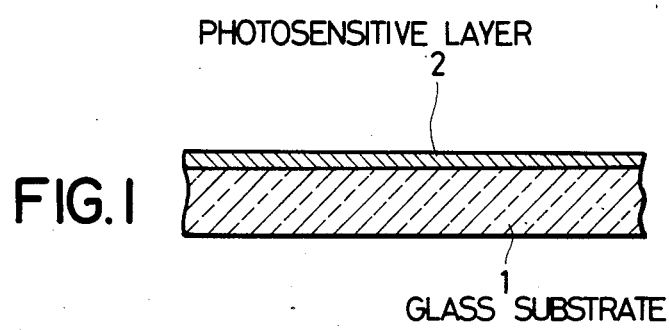
FIG. 1 is a greatly enlarged cross-sectional view of an optical recording medium according to the present invention.

The present invention will be described in detail by way of the following examples.

EXAMPLE 1

Preparation of 5'-Dimethylamino-1',3',3'-Trimethyl-6-Nitrospiro(2H-1-Benzothiopyran-2,2'-Indoline)

The subject of this Example, falling under the general formula (I), is the following compound:

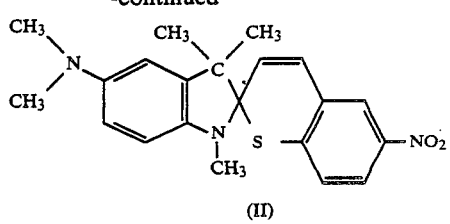

(II)

The compound represented by formula (II) was prepared in accordance with the following reaction route:

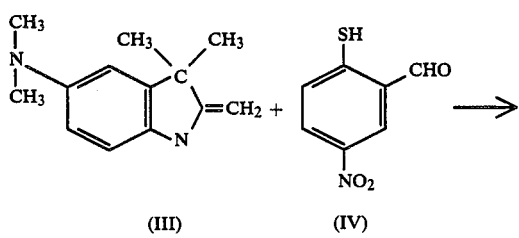

(III)     (IV)

-continued

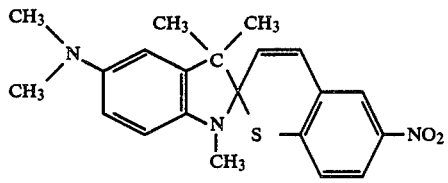

(II)

5-dimethylamino-1,3,3-trimethyl-2-methyleneindoline given by formula (III) was prepared as follows. The reaction proceeds in accordance with the following scheme:

(A)

5-amino-2,3,3-trimethylindolenine (3.74 g), 1,2,2,6,6-pentamethylpiperidine (6.61 g) and methyl iodide (18.27 g) were dissolved together in DMF (dimethylformamide) (40 cc) and reacted at room temperature for 15 hours. The resulting crystalline material was washed with an acetone solution containing 6% DMF, and with acetone and then dried. The dried crystals were added to n-propyl alcohol (150 cc) containing metallic sodium (2.35 g) and then subjected to reflux and demethylation for 17 hours. N-propyl alcohol was removed at a reduced pressure. Water was added to the residue, and the resultant mixture was extracted with ether. After the ether was removed, 5-dimethylamino-1,3,3-trimethyl-2-methyleneindoline (4.21 g; 87% yield) represented by formula (III) was obtained.

Another starting material, 5-nitrothiosalicylaldehyde represented by formula (IV), was synthesized in accordance with the following scheme:

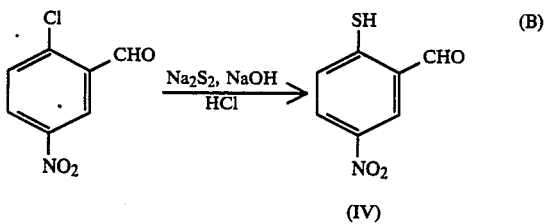

2-chloro-5-nitrobenzaldehyde (5 g) was added to ethanol (10 cc), and the mixture was heated and refluxed. A mixture of Na$_2$S.9H$_2$O (4.66 g) and S (0.62 g) was heated to prepare Na$_2$S$_2$. The resultant Na$_2$S$_2$ was added to a boiling 2-chloro-5-nitrobenzaldehyde solution in ethanol over 15 minutes. A 95% ethanol solution (10 cc) containing NaOH (1.08 g) was added to the resultant mixture over 30 minutes. The mixture was cooled and mixed with ice water (30 g of ice and 400 cc of water) and an insoluble residue was filtered off. The filtrate was neutralized with an HCl solution, and a yellow precipitate was obtained. The precipitate was collected by filtration and was dissolved with heating in a 95% ethanol solution containing NaOH (1.08 g). The insoluble residue was removed by filtration, and the filtrate was neutralized again with HCl. The resultant mixture was cooled to yield yellow crystal (3.15 g; 64% yield) of 5-nitrothiosalicylaldehyde represented by formula (IV). The melting point of the yellow crystal was 85° C. to 88° C.

The resultant indoline (3 g) represented by formula (III) and thiosalicylaldehyde (3 g) represented by formula (IV) were heated and refluxed in ethanol (40 cc) for one hour, and the ethanol was then removed. The residue was refined by column chromatography (using a silica gel column), thus yielding the desired indolinospirobenzothiopyran compound represented by formula (II). The compound was further recrystallized from a methanol-chloroform mixed solvent. In this case, the yield of the resultant compound was 2.4 g (or 45%) and the compound had a melting point of 166.5° C. to 167° C. The structure of the compound represented by formula (II) was confirmed by infrared, nuclear magnetic resonance, and mass spectroscopy:

Mass Spectrum:
measured mass: 381.148,
calculated mass: 381.151,
empirical formula: C$_{21}$H$_{23}$N$_3$O$_3$S.

PREPARATION OF OPTICAL RECORDING MEDIUM 40 parts by weight of the indolinospirobenzothiopyran compound represented by formula (II) and 100 parts by weight of a vinyl chloride-vinylidene chloride copolymer (Denkavinyl #1000W obtained from Denki Kagaku Kogyo K.K.) were dissoved in a mixed solvent consisting of 500 parts by weight of cyclohexanone and 500 parts by weight of tetrahydrofuran. The resultant solution was coated on a glass substrate to prepare a sample having a 1.2 micron thick photosensitive layer.

A structure is illustrated in FIG. 1, which illustrates a glass substrate 1 having a photosensitive layer 2 formed thereon.

Ultraviolet rays were allowed to irradiate through an ultraviolet transmission filter UV-D33S (available from Toshiba Glass K.K.) from a 500W-ultra high-pressure mercury lamp (available from Ushio Denki Inc.) to the photosensitive layer 2 until the layer 2 was completely colored by the ultraviolet rays. The photosensitive layer 2 changed to dark black upon saturation and had an absorption maximum (λmax) of 580 nm. At this point, the absorbance of the layer 2 was 0.97. The colored sample was heated at a temperature of 100° C. for one hour. The color of the photosensitive layer 2 was changed to reddish purple and its absorption maximum, λmax, was 530 nm. In this case, the absorbance was 0.81. The resultant optical recording medium sample was not degraded at room temperature after 6 months had elapsed. The absorbance of the layer 2 did not change even when it was irradiated with visible light having a wavelength longer than 420 nm at an intensity of 160 mW/cm$^2$ for 10 minutes. The absorbance measurement was made using a self-recording spectrophotometer Model 320 available from Hitachi Ltd.

COMPARATIVE EXAMPLE 1

A sample was prepared in the same manner as Example 1 except that 1',3',3'-trimethyl-6-nitrospiro(2H-1-benzopyran-2,2'-indoline) represented by formula (V) was used in place of the compound represented by formula (II) used in Example 1:

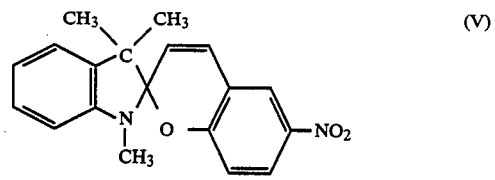

The absorption maximum in the absorption curve for the sample colored upon irradiation of ultraviolet rays was 585 nm, and the absorbance at 585 nm was 1.45. The layer was substantially completely discolored within 30 seconds when the layer was heated to 100° C. When the layer was irradiated with visible light under the same conditions as in Example 1 after coloring of the layer, the layer was substantially completely discolored within about 30 seconds.

EXAMPLES 2-12

Compounds of general formula (I) listed in Table 1 were prepared in the same manner as in Example 1 to provide optical recording medium samples. However, in Examples 9 to 12, a phenolic resin (PSK-2320 from Gun-ei Kagaku Kogyo K.K.) was used as the binder resin, and 1,000 parts by weight of cyclohexanone were used as a solvent. Some of the data of the optical recording medium of Example 1 were included in Table 1. Measurements of the absorbances of the layers immediately after ultraviolet irradiation and after heat treatment were performed in the same manner as in Example 1.

As can be seen from the data in Table 1, the heat-treated optical recording media of the present invention have high absorbances and are thermally stable.

Figure 2:
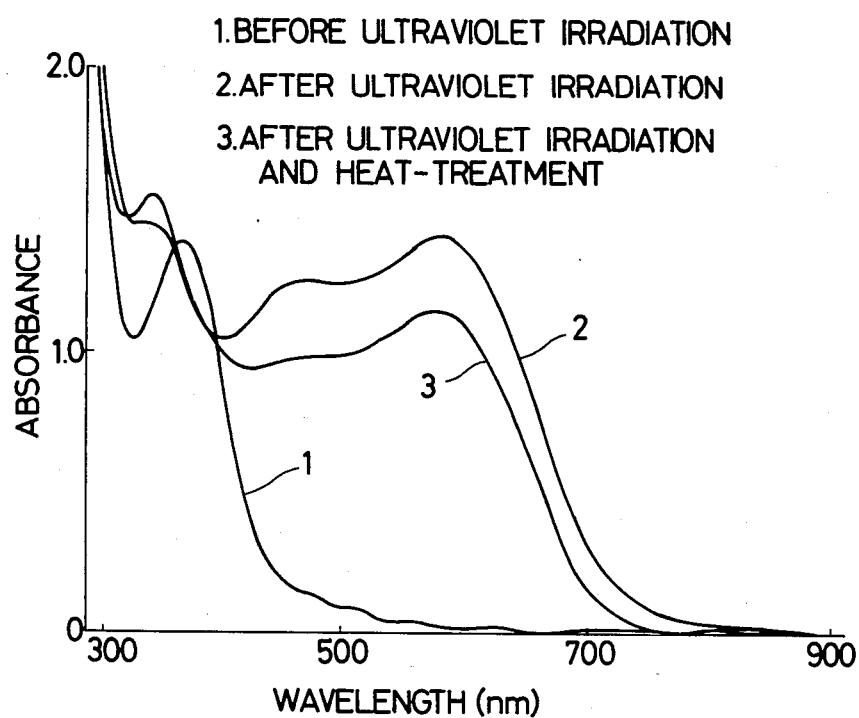
FIG. 2 is a graph showing the absorption spectra of the optical recording medium samples before and after ultraviolet irradiation, and after ultraviolet irradiation followed by heat treatment.

The absorption spectra of the photosensitive layer of the sample in Example 9 were measured to obtain an absorption spectrum before ultraviolet irradiation (curve 1), an absorption spectrum immediately after ultraviolet irradiation (curve 2) and an absorption spectrum after ultraviolet irradiation and heat treatment (100° C. for one hour) (curve 3) were obtained. It can be seen from FIG. 2 that the components having high absorbance are still left in the optical recording medium after heat treatment.

EXAMPLE 13

5'-dimethylamino-1',3',3'-trimethyl-6-nitro-7-methoxyspiro(2H-1-benzothiopyran-2,2'-indoline) represented by formula (VI):

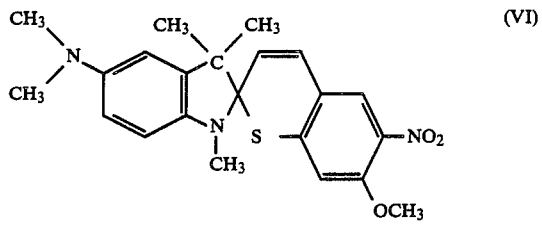

(VI)

and used in Example 2 in Table 1 was prepared. A mask having an image pattern was placed on the photosensitive layer, and the layer was irradiated with ultraviolet rays through the mask. The image pattern was transferred to the photosensitive layer, and the sample was heated at a temperature of 100° C. for one hour. An optical recording medium having a clear image and the same high contrast as that before heat treatment could be obtained. The image did not degrade when 6 months and more had elapsed.

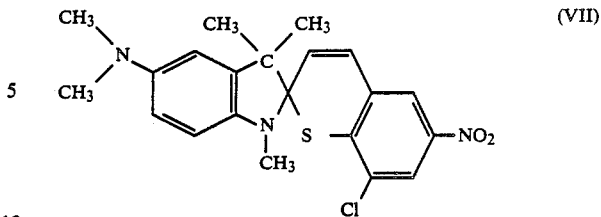

Figure 3:
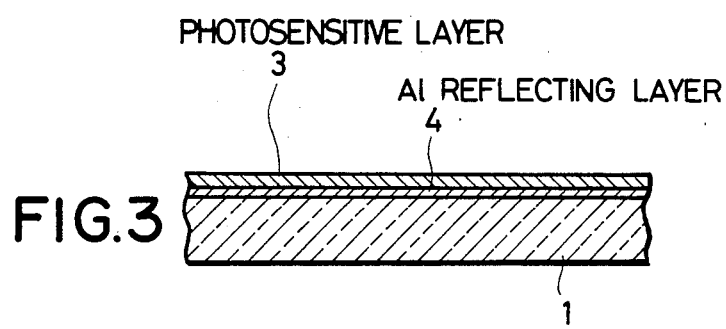
FIG. 3 is a greatly enlarged cross-sectional view of a modified form of the present invention.

(VII)

used in Examples 8 and 9 in the Table and 100 parts by weight of the phenolic resin mentioned in a previous Example were used. These materials were dissolved in 1,000 parts by weight of cyclohexanone. The resultant solution was spin-coated on an aluminum reflecting layer 4 formed on a glass substrate 1 and was dried to form a 1.2-micron thick photosensitive layer 3 as shown in FIG. 3. The layer 3 was irradiated with ultraviolet rays through a mask having an image pattern for 5 minutes. The exposed layer 3 was heated to a temperature of 100° C. for one hour. The same image pattern (i.e., a negative image) as in the mask was clearly transferred to the photosensitive layer 3. Reflectances of the photosensitive layer 3 were measured with an He-Ne laser beam focused to a spot size of about 1 micron. The reflectance of the image portion was 3% and that of the nonimage portion was 78%, thus giving high contrast.

EXAMPLE 15

50 parts by weight of 5'-dimethylamino-1',3',3'-

TABLE 1

| | Compound Represented by General Formula (I) | | | | | Immediately After Ultraviolet Irradiation | | After Ultraviolet Irradiation and Heat Treatment | |
|---|---|---|---|---|---|---|---|---|---|
| Example | $R_1$ | $R_2$ | $R_3$ | Melting Point (°C.) | Binder Resin | λmax (nm) | Absorbance | λmax (nm) | Absorbance |
| 1 | H | H | H | 166.5-167 | Vinyl chloridevinylidene | 580 | 0.97 | 530 | 0.81 |
| 2 | H | $OCH_3$ | H | 184-185 | chloride copolymer | 520 | 1.01 | 530 | 0.98 |
| 3 | H | H | $OCH_3$ | 187-187.5 | (Denka-vinyl #1000: | 600 | 0.80 | 520 | 0.60 |
| 4 | H | H | $CH_2OC_2H_5$ | 151.5-153.5 | trade mark of Denki | 600 | 0.80 | 520 | 0.64 |
| 5 | Cl | H | H | 170-172 | Kagaku Kogyo K.K.) | 660 | 0.44 | 500 | 0.60 |
| 6 | H | H | $CH_3$ | 156-156.5 | | 620 | 0.60 | 510 | 0.79 |
| 7 | H | H | Br | 206-208 | | 620 | 0.87 | 480 | 0.76 |
| 8 | H | H | Cl | 209-211 | | 620 | 0.96 | 480 | 0.80 |
| 9 | H | H | Cl | 209-211 | Phenol resin (PSK-2320: | 580 | 1.40 | 570 | 1.14 |
| 10 | H | H | $CH_2OH$ | 117.5-119 | trade mark of Gun-ei | 580 | 1.66 | 570 | 1.50 |
| 11 | H | H | $CH_2OC(CH_3)_3$ | 153-154 | Kagaku Kogyo K.K.) | 570 | 1.27 | 560 | 1.10 |
| 12 | H | H | $CH_2N\langle\rangle$ | 158-159.5 | | 590 | 1.37 | 570 | 1.38 |

EXAMPLE 14

40 parts by weight of 5'-dimethylamino-1',3',3'-trimethyl-6-nitro-8-chlorospiro(2H-1-benzothiopyran-2,2'-indoline) represented by the formula (VII):

trimethyl-6-nitro-8-hydroxymethylspiro (2H-1-benzothiopyran-2,2'-indoline) represented by formula (VIII):

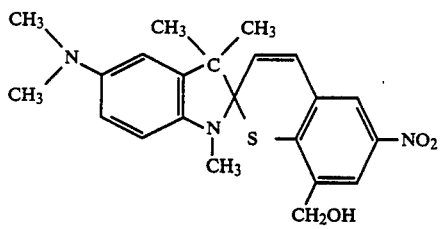

Figure 4:
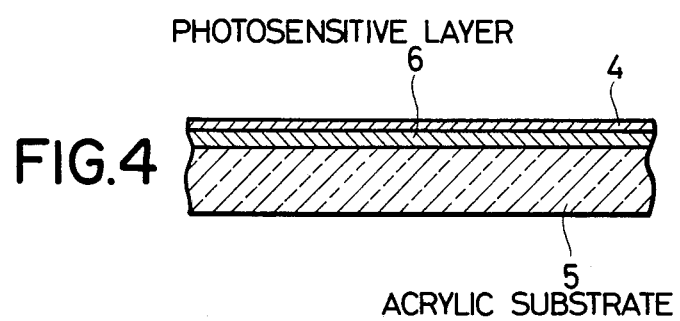
FIG. 4 is a greatly magnified cross-sectional view of a still further modified form of the invention.

(VIII)

and used in Example 10 were dissolved together with 100 parts by weight of a phenolic resin (PSK-4300 from Gun-ei Kagaku Kogyo K.K.) in 600 parts by weight of cyclohexanone. The resultant solution was coated on a yellow, ultraviolet-shielding acrylic substrate 5 to form a 1.6-micron thick photosensitive layer 6 as shown in FIG. 4. The layer 6 was irradiated with ultraviolet rays emitted through a UV filter and through a mask having an image pattern from a 500 W-ultra high-pressure mercury lamp. The image pattern was thus transferred to the layer 6, and the exposed layer 6 was heated at a temperature of 100° C. for one hour. An aluminum reflecting layer 4 was deposited on the transferred photosensitive layer 6. Reflectances of the layer 6 were measured with an He-Ne laser with a 1-micron beam spot from the side of the acrylic layer 5. The reflectance of the nonimage portion was 73% and the reflectance of the image portion was 3%, thus giving a high contrast. Since the photosensitive layer 6 was sandwiched between the acrylic substrate 5 (i.e., the ultraviolet shielding substrate) and the aluminum reflecting layer, further irradiation of ultraviolet rays to the optical recording medium did not cause coloration of the nonimage portin of the photosensitive layer 6. The optical recording medium in this Example was stable against heat and visible light. Even when the layer was irradiated with visible light having a wavelength greater than 500 nm at 200 to 300 $J/cm^2$, no change in contrast was observed.

EXAMPLE 16

5'-dimethylamino-1',3',3'-trimethyl-6-nitro-8-hydroxymethylspiro(2H-1-benzothiopyran-2,2'-indoline) used in Example 15 was used to prepare a solution having the following composition:

| Spirobenzothiopyran compound: | 75 parts by weight |
| --- | --- |
| Cobalt naphthenate | 20 parts by weight |
| Phenol resin (PSK-2320: trade mark of Gun-ei Kagaku Kogyo K. K.) | 100 parts by weight |
| Cyclohexanone | 600 parts by weight |

The resultant solution was coated on a yellow, ultraviolet shielding acrylic substrate to form a 1.8 -micron thick photosensitive layer. The layer was irradiated with ultraviolet rays through a mask in the same manner as in Example 15, and the image was transferred to the layer. The layer with the image was heated to a temperature of 100° C. for one hour and an aluminum reflecting layer was deposited thereover. The layer was then irradiated with an He-Ne laser with a beam spot of 1 micron from the substrate side. The reflectance of the nonimage portion was 70% and that of the image portin was 3%, thus giving a high contrast. Even when the optical recording medium was irradiated with visible light at a wavelength of greater than 500 nm, and having an intensity of 250 $mW/cm^2$ for 10 hours (10,000 $J/cm^2$), the reflectance distribution of the photosensitive layer did not change.

The optical recording medium of the present invention has a photosensitive layer containing as an effective component an indolinospirobenzothiopyran compound having a dimethyl-amino group in the 5'-position. Since the photosensitive layer recorded with the colored image upon irradiation of ultraviolet rays was heat-treated to stabilize the colored image against heat and visible light, the optical recording medium of the present invention can be used in a variety of long-term applications such as memory devices and copying devices and can also be applied to the field of display for enlarging and projecting an image upon irradiation of visible light.

The image formed by the photosensitive layer of the optical recording medium of the present invention does not have any particle structure but can be obtained upon photochromatic change of the indolinospirobenzothiopyran molecules themselves, thereby providing a high degree of resolution. Recording can be performed in microdots with ultraviolet rays. The colored portion has a high absorbance at 600 to 700 nm. Therefore, since the colored pattern can be read with a laser or light-emitting diode which has such long wavelengths, the optical recording medium of the present invention can be used for optical cards and the like.

It will be evident that various modifications can be made to the described embodiments without departing from the scope of the present invention.

We claim as our invention:

1. An optical recording medium comprising a substrate and a photosensitive layer thereon, said photosensitive layer containing for every 100 parts by weight of a polymeric binder resin from 20 to 120 parts by weight of an indolinospirobenzothiopyran compound represented by the general formula (I):

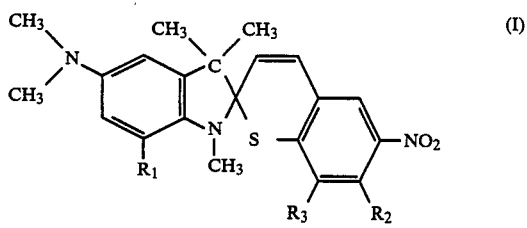

(I)

wherein $R_1$, $R_2$ are a hydrogen atom, a halogen atom, an alkyl group having from 1 to 5 carbon atoms, an alkoxy group containing from 1 to 5 carbon atoms, an alkoxyethyl group containing from 1 to 5 carbon atoms in the alkoxy group, a hydroxymethyl group or an alkylaminomethyl group containing 2 to 6 carbon atoms in the alkyl group, and $R_3$ is an alkylaminomethyl group containing 2 to 6 carbon atoms in the alkyl group.

2. A medium according to claim 1 wherein the polymeric binder resin material is a chlorine-containing polymer.

3. A medium according to claim 2 wherein the chlorine-containing polymer is a vinyl chloride-vinylidene chloride copolymer.

4. A medium according to claim 1 wherein the polymeric material is a phenolic resin.

5. A medium according to claim 1, wherein the photosensitive layer further contains a photocuring agent.

6. A medium according to claim 1 wherein the photosensitive layer further contains a heat-curing agent.

7. A medium according to claim 1 wherein the photosensitive layer is formed on a base and is provided with a metal reflecting layer on one of the major surfaces thereof.

8. A medium according to claim 7 wherein the photosensitive layer has been heat-treated after coloring of the photosensitive layer by irradiation with ultraviolet rays in a predetermined pattern.

9. A medium according to claim 8 wherein the photosensitive layer is formed on a transparent base of an ultraviolet shielding material, and a metal reflecting layer is formed on the photosensitive layer.

* * * * *